(12) United States Patent
Bikfalvi et al.

(10) Patent No.: US 8,481,033 B2
(45) Date of Patent: Jul. 9, 2013

(54) NEUTRALIZING ANTIBODIES AND FRAGMENTS THEREOF DIRECTED AGAINST PLATELET FACTOR-4 VARIANT 1 (PF4V1)

(75) Inventors: Andreas Bikfalvi, Talence (FR); Alexandre Dubrac, Talence (FR); Eric Lacazette, Toulouse Cedex 4 (FR); Herve Prats, Toulouse Cedex 4 (FR)

(73) Assignee: INSERM (Institute National de la Santé et de la Recherche Médicale), Paris (FR)

( * ) Notice: Subject to any disclaimer, the term of this patent is extended or adjusted under 35 U.S.C. 154(b) by 0 days.

(21) Appl. No.: 13/122,468

(22) PCT Filed: Oct. 7, 2009

(86) PCT No.: PCT/EP2009/063005
§ 371 (c)(1),
(2), (4) Date: Jun. 22, 2011

(87) PCT Pub. No.: WO2010/040766
PCT Pub. Date: Apr. 15, 2010

(65) Prior Publication Data
US 2011/0250210 A1    Oct. 13, 2011

(30) Foreign Application Priority Data
Oct. 7, 2008    (EP) .................................... 08305648

(51) Int. Cl.
*A61K 39/00*    (2006.01)
(52) U.S. Cl.
USPC .................. 424/139.1; 424/141.1; 424/145.1; 514/13.3

(58) Field of Classification Search
None
See application file for complete search history.

(56) References Cited

U.S. PATENT DOCUMENTS 5,068,178 A * 11/1991 Nowinski ....................... 435/7.2
5,272,059 A * 12/1993 Schlaeppi et al. ............. 435/7.9

FOREIGN PATENT DOCUMENTS

| WO | 90/08824 | 8/1990 |
| WO | 2006/029487 | 3/2006 |
| WO | WO 2006029487 A2 * | 3/2006 |

OTHER PUBLICATIONS

Struyf et al., Circ Res. Oct. 29, 2004;95(9):855-7. Epub Sep. 30, 2004.*
Stanker et al., J Immunol. Jun. 1, 1986;136(11):4174-80.*
Wikipedia printout for "Primates", downloaded Aug. 23, 2012, 28 pages.*
Green et al., Mol. Cell. Biol., 9(4):1445-1451 (1989).
Lasagni et al., Blood, 109(10):4127-4134 (2007).
Lozano et al., J. Biol. Chem., 276(38):35723-35734 (2001).
Struyf et al., Circulation Res., 95(9):855-857 (2004).
Vandercappellen et al., J. Leukocyte Biology, 82(6):1519-1530 (2007).
Dubrac et al., Blood, 116(22):4703-4711 (2010).
International Search Report and Written Opinion in PCT/EP2009/063005, dated Nov. 27, 2009.
Struyf et al., Cancer Res., 67(12):5940-5948 (2007).

* cited by examiner

*Primary Examiner* — Michael Szperka
(74) *Attorney, Agent, or Firm* — McAndrews, Held & Malloy, Ltd.

(57) ABSTRACT

The present invention relates to neutralizing antibodies and fragments thereof directed against Platelet Factor-4 variant 1 (PF4v1) and their use for treating pathologies that require induction of angiogenesis or diseases associated with pathological angiogenesis.

5 Claims, 9 Drawing Sheets

Figure 4:
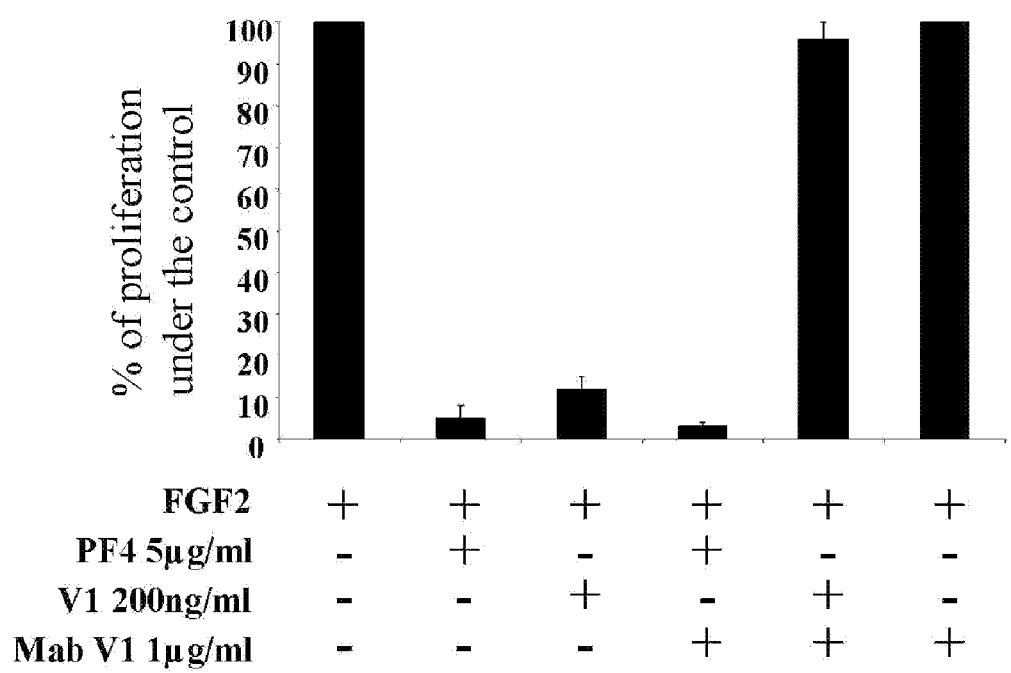

A
```
                  20                              40
                   |                               |
PF4  EAEEDGDLQCLCVKTTSQVRPRHITSLEVIKAGPHCPTAQ 40
V1   EAEEDGDLQCLCVKTTSQVRPRHITSLEVIKAGPHCPTAQ 40
                       60
                        |
     LIATLKNGRKICLDLQAPLYKKIIKKLLES* 71
     LIATLKNGRKICLDLQALLYKKIIKEHLES* 71
```
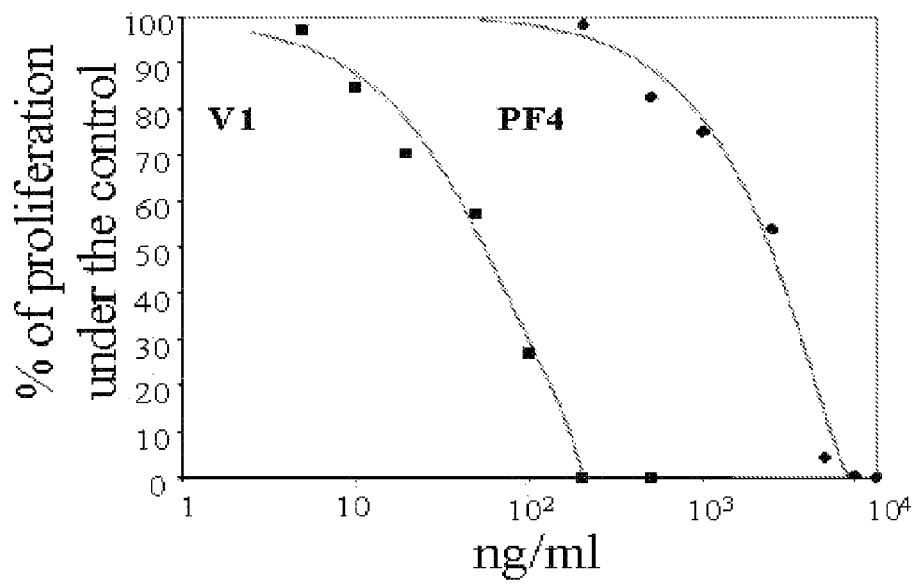
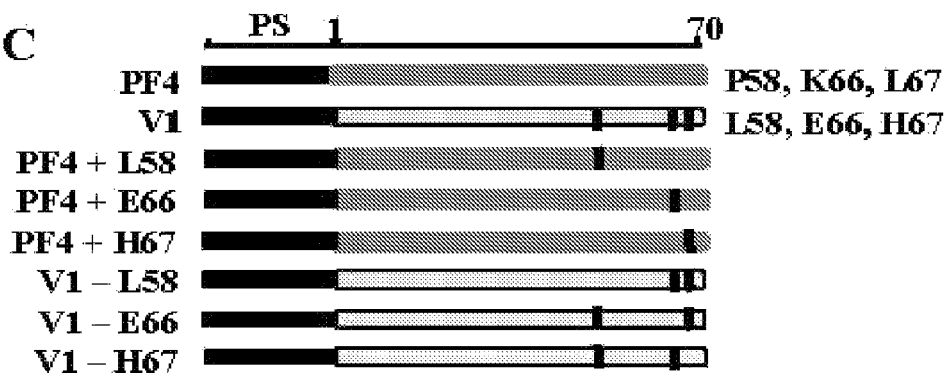
Figure 1

A
B
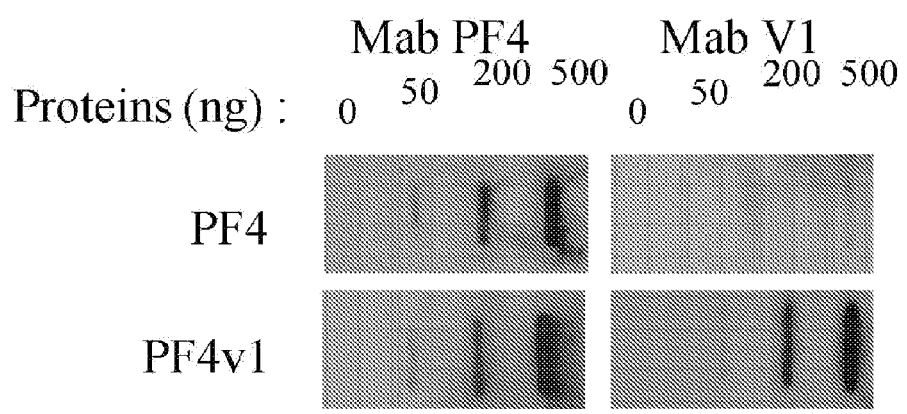
C
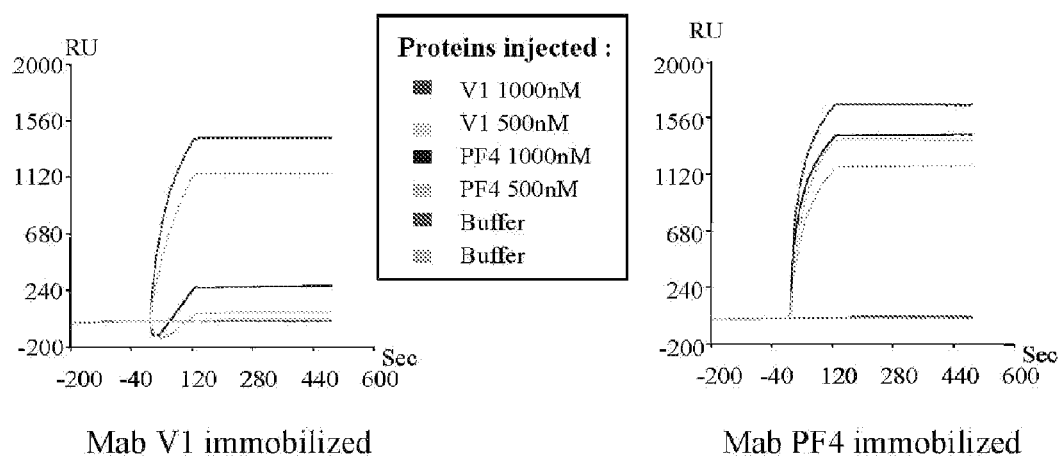
Figure 2

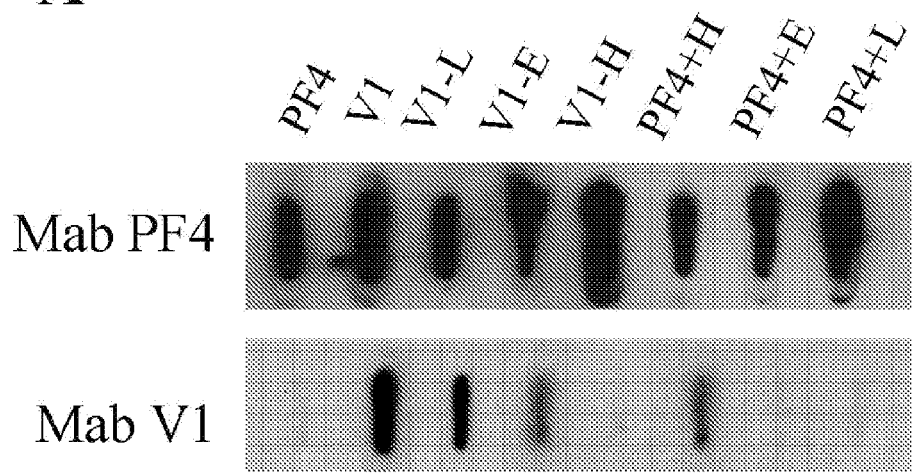
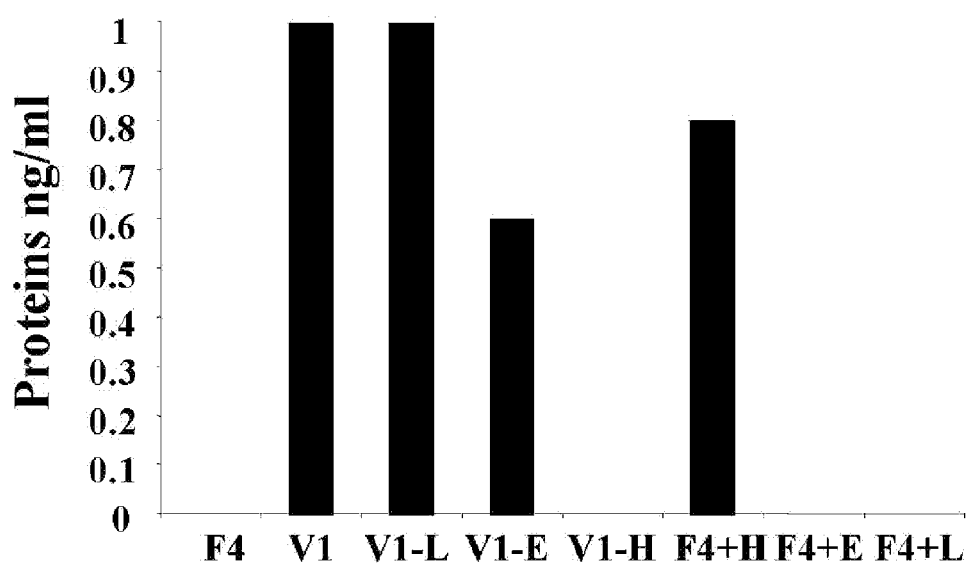
Figure 3

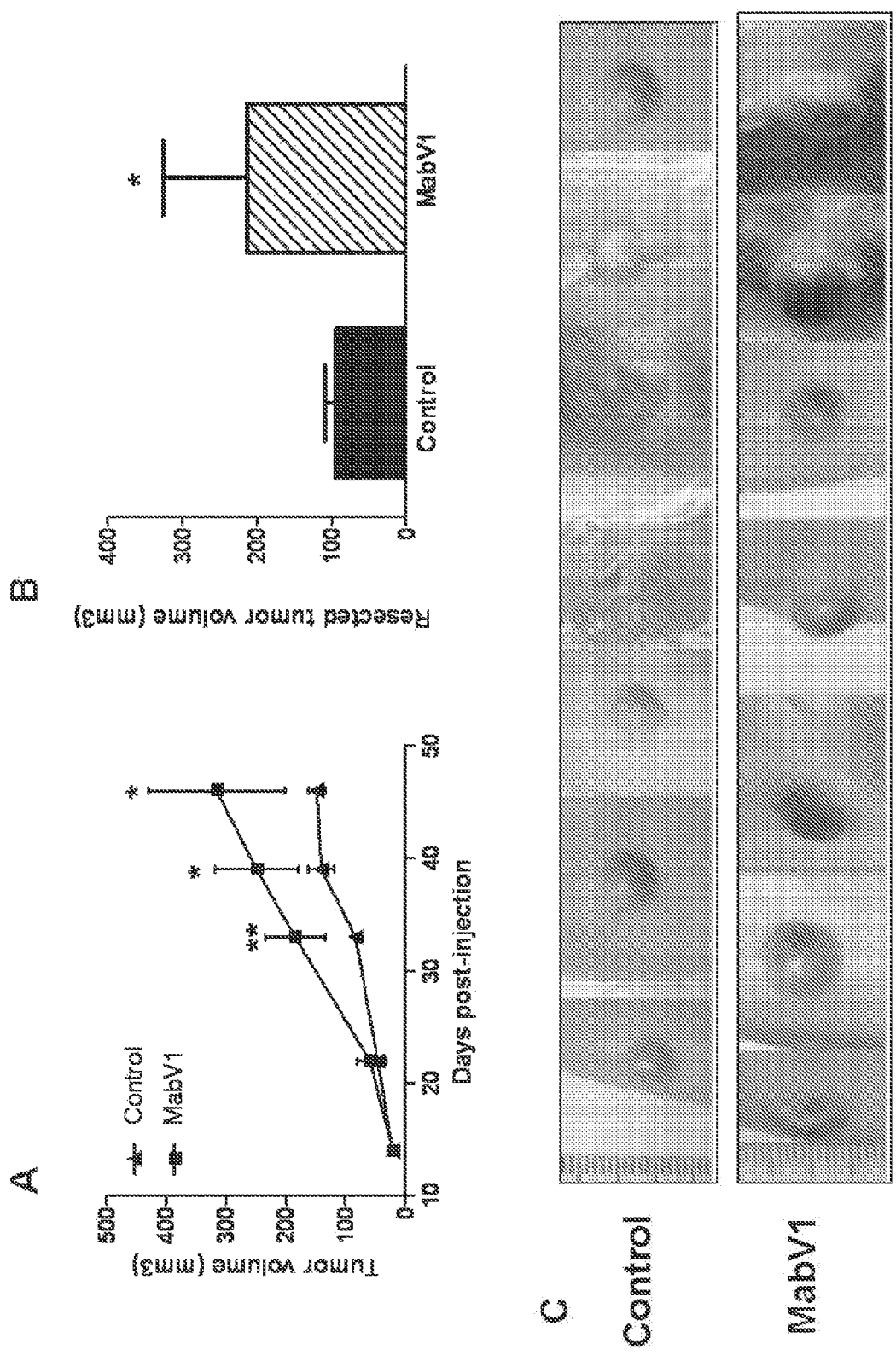
Figure 5A-B-C

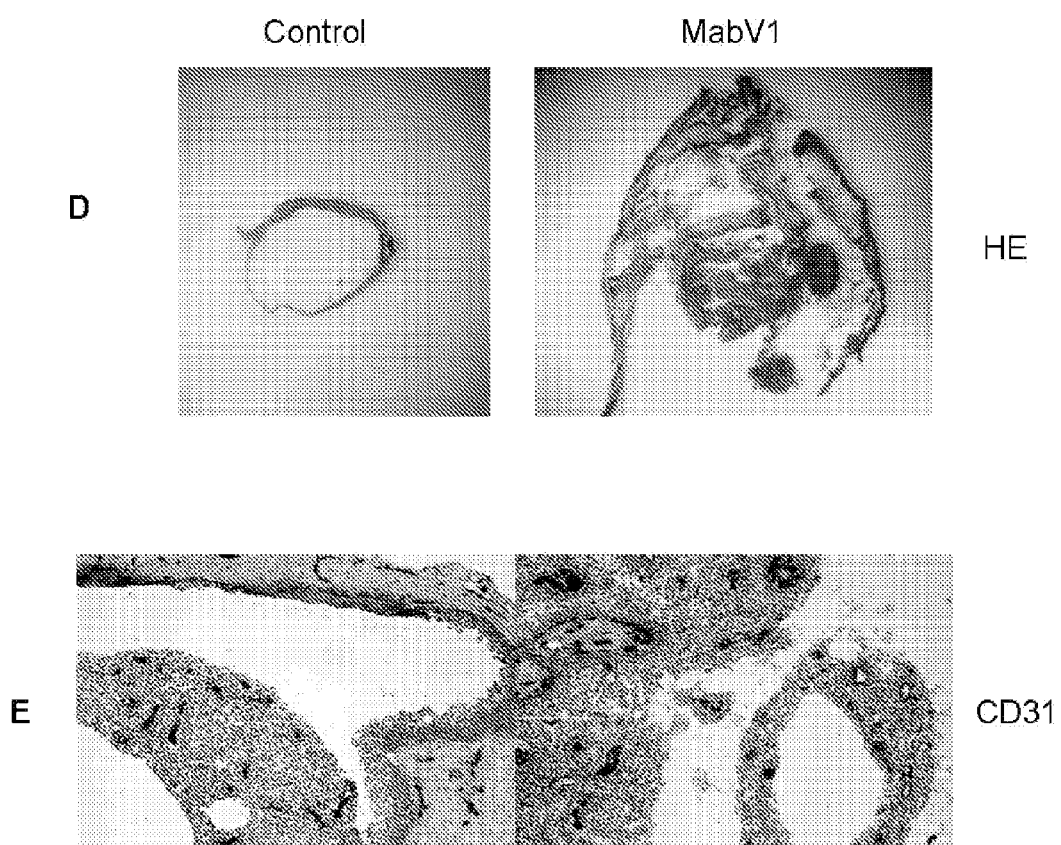
Figure 5D-E

Figure 7

SEQUENCE LISTING

```
<160> NUMBER OF SEQ ID NOS: 19

<210> SEQ ID NO 1
<211> LENGTH: 70
<212> TYPE: PRT
<213> ORGANISM: Homo sapiens

<400> SEQUENCE: 1

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Leu Leu Tyr Lys Lys Ile Ile
    50                  55                  60

Lys Glu His Leu Glu Ser
65                  70

<210> SEQ ID NO 2
<211> LENGTH: 36
<212> TYPE: DNA
<213> ORGANISM: artificial
<220> FEATURE:
<223> OTHER INFORMATION: primer

<400> SEQUENCE: 2
aaaaaactca agatctggta ccatgagctc cgcagc                              36

<210> SEQ ID NO 3
<211> LENGTH: 41
```

```
<212> TYPE: DNA
<213> ORGANISM: artificial
<220> FEATURE:
<223> OTHER INFORMATION: primer

<400> SEQUENCE: 3
aaaaaaccgc ggccgcggat ccccctaact ctccaaaagt t                 41

<210> SEQ ID NO 4
<211> LENGTH: 36
<212> TYPE: DNA
<213> ORGANISM: artificial
<220> FEATURE:
<223> OTHER INFORMATION: primer

<400> SEQUENCE: 4
aaaaaactca agatctggta ccatgagctc cgcagc                       36

<210> SEQ ID NO 5
<211> LENGTH: 41
<212> TYPE: DNA
<213> ORGANISM: artificial
<220> FEATURE:
<223> OTHER INFORMATION: primer

<400> SEQUENCE: 5
aaaaaaccgc ggccgcggat ccccctaact ctccaaatgt t                 41

<210> SEQ ID NO 6
<211> LENGTH: 37
<212> TYPE: DNA
<213> ORGANISM: artificial
<220> FEATURE:
<223> OTHER INFORMATION: primer

<400> SEQUENCE: 6
aaacaattgg tcatatggaa gctgaagaag atgggga                      37

<210> SEQ ID NO 7
<211> LENGTH: 41
<212> TYPE: DNA
<213> ORGANISM: artificial
<220> FEATURE:
<223> OTHER INFORMATION: primer

<400> SEQUENCE: 7
aaaaaaccgc ggccgcggat ccccctaact ctccaaaagt t                 41

<210> SEQ ID NO 8
<211> LENGTH: 37
<212> TYPE: DNA
<213> ORGANISM: artificial
<220> FEATURE:
<223> OTHER INFORMATION: primer

<400> SEQUENCE: 8
aaacaattgg tcatatggaa gctgaagaag atgggga                      37

<210> SEQ ID NO 9
<211> LENGTH: 41
<212> TYPE: DNA
<213> ORGANISM: artificial
<220> FEATURE:
<223> OTHER INFORMATION: primer

<400> SEQUENCE: 9
aaaaaaccgc ggccgcggat ccccctaact ctccaaatgt t                 41
```

<210> SEQ ID NO 10
<211> LENGTH: 40
<212> TYPE: DNA
<213> ORGANISM: artificial
<220> FEATURE:
<223> OTHER INFORMATION: primer

<400> SEQUENCE: 10
gcttggatct gcaagccccg ctgtacaaga aaatcattaa                           40

<210> SEQ ID NO 11
<211> LENGTH: 40
<212> TYPE: DNA
<213> ORGANISM: artificial
<220> FEATURE:
<223> OTHER INFORMATION: primer

<400> SEQUENCE: 11
ttaatgattt tcttgtacag cggggcttgc agatccaagc                           40

<210> SEQ ID NO 12
<211> LENGTH: 40
<212> TYPE: DNA
<213> ORGANISM: artificial
<220> FEATURE:
<223> OTHER INFORMATION: primer

<400> SEQUENCE: 12
gctgtacaag aaaatcatta agaaacattt ggagagttag                           40

<210> SEQ ID NO 13
<211> LENGTH: 40
<212> TYPE: DNA
<213> ORGANISM: artificial
<220> FEATURE:
<223> OTHER INFORMATION: primer

<400> SEQUENCE: 13
ctaactctcc aaatgtttct taatgatttt cttgtacagc                           40

<210> SEQ ID NO 14
<211> LENGTH: 40
<212> TYPE: DNA
<213> ORGANISM: artificial
<220> FEATURE:
<223> OTHER INFORMATION: primer

<400> SEQUENCE: 14
gctgtacaag aaaatcatta aggaactttt ggagagttag                           40

<210> SEQ ID NO 15
<211> LENGTH: 40
<212> TYPE: DNA
<213> ORGANISM: artificial
<220> FEATURE:
<223> OTHER INFORMATION: primer

<400> SEQUENCE: 15
ctaactctcc aaaagttcct taatgatttt cttgtacagc                           40

<210> SEQ ID NO 16
<211> LENGTH: 40
<212> TYPE: DNA
<213> ORGANISM: artificial
<220> FEATURE:
<223> OTHER INFORMATION: primer

```
<400> SEQUENCE: 16
gctgtacaag aaaatcatta agaaactttt ggagagttag                              40

<210> SEQ ID NO 17
<211> LENGTH: 40
<212> TYPE: DNA
<213> ORGANISM: artificial
<220> FEATURE:
<223> OTHER INFORMATION: primer

<400> SEQUENCE: 17
ctaactctcc aaaagtttct taatgatttt cttgtacagc                              40

<210> SEQ ID NO 18
<211> LENGTH: 70
<212> TYPE: PRT
<213> ORGANISM: Homo sapiens

<400> SEQUENCE: 18

Glu Ala Glu Glu Asp Gly Asp Leu Gln Cys Leu Cys Val Lys Thr Thr
 1               5                  10                  15

Ser Gln Val Arg Pro Arg His Ile Thr Ser Leu Glu Val Ile Lys Ala
             20                  25                  30

Gly Pro His Cys Pro Thr Ala Gln Leu Ile Ala Thr Leu Lys Asn Gly
         35                  40                  45

Arg Lys Ile Cys Leu Asp Leu Gln Ala Pro Leu Tyr Lys Lys Ile Ile
     50                  55                  60

Lys Lys Leu Leu Glu Ser
 65                  70

<210> SEQ ID NO 19
<211> LENGTH: 19
<212> TYPE: PRT
<213> ORGANISM: Homo sapiens

<400> SEQUENCE: 19

Cys Leu Asp Leu Gln Ala Leu Leu Tyr Lys Lys Ile Ile Lys Glu His
 1               5                  10                  15

Leu Glu Ser
```

US 8,481,033 B2

NEUTRALIZING ANTIBODIES AND FRAGMENTS THEREOF DIRECTED AGAINST PLATELET FACTOR-4 VARIANT 1 (PF4V1)

The present application is filed pursuant to 35 U.S.C. 371 as a U.S. National Phase application of International Patent Application No. PCT/EP09/63005, which was filed Oct. 7, 2009, claiming the benefit of priority to European Patent Application No. 08305648.1, which was filed on Oct. 7, 2008. The entire text of the aforementioned applications is incorporated herein by reference in its entirety.

FIELD OF THE INVENTION

The present invention relates to neutralizing antibodies and fragments thereof directed against Platelet factor variant 1 (PF4v1) and their use for treating pathologies that require induction of angiogenesis or diseases that are associated with pathological angiogenesis and for detecting PF4v1 in a biological sample.

BACKGROUND OF THE INVENTION

Angiogenesis, the development of new blood vessels, is a complex biological process which occurs both in physiological conditions, such as during embryonic development, wound healing etc., and in pathological conditions, such as cancer (Bikfalvi and Bicknel, 2002). Angiogenesis is controlled by the net balance between pro-angiogenic and anti-angiogenic factors. Known factors for promoting angiogenesis are for example the fibroblast growth factor (FGF) family, Vascular Endothelial Growth Factor (VEGF), Platelet-Derived Growth Factor (PDGF) and the angiopoetins. Factors which inhibit angiogenesis have been the focus of many anti-cancer research projects since it was postulated that tumors need to be vascularised in order to grow and that diffusible molecules regulate this process (see for example Auguste et al., 2005 for review). Anti-angiogenic molecules include antibodies such as avastatin, small chemical molecules, and endogenous factors, among which Platelet Factor 4 (PF4).

The CXC-chemokine family consists of pro-inflammatory cytokines, primarily involved in chemoattraction and activation of specific leukocytes in various immuno-inflammatory responses. The CXC chemokine family is unique because it comprises angiogenic and angiostatic chemokines. The Platelet Factor 4 (PF4 or CXCL4) was the first chemokine described as a regulator of angiogenesis (Maione T E et al. 1990). PF4 was previously known as oncostatin as described in the international patent application WO 85/04397.

At the same time, the gene of a nonallelic PF4-variant, called PF4v1 or CXCL4L1 was also identified. The mature proteins differ in only three amino acids located in the C-terminus (P58L, K66E, and L67H) in PF4 and PF4v1, respectively (Eisman R et al. 1990). PF4v1 was characterised as a potent inhibitor of angiogenesis more effective than PF4. Thus, the international patent application WO 2006/029487 relates to PF4v1, fragments, and modified versions of PF4v1 and PF4v1 fragments for the prevention and/or reduction of angiogenesis, and more particularly for the treatment or prevention of angiogenic disorders or diseases involving angiogenic disorders or pathological angiogenesis such as cancer.

In contrast to the many studies focused on the search for anti-angiogenic compounds, very few approaches have been developed to induce angiogenesis. Therefore, there is still a need in the art for methods for inducing angiogenesis.

SUMMARY OF THE INVENTION

The inventors have developed novel neutralizing antibodies which specifically recognize PF4v1 and which block its anti-angiogenic activity.

The inventors have demonstrated for the first time that amongst the three different amino acids between PF4 and PF4v1, only histidine 67 is responsible for the more effective inhibition of angiogenesis of PF4v1. They have also shown that only antibodies specifically recognizing histidine residue at position 67 of PF4v1 abolish the gain of function of PF4v1 on PF4.

Thus, a first aspect of the invention relates to a neutralizing antibody directed against Platelet factor variant 1 (PF4v1) or a fragment thereof, wherein said antibody or said fragment recognizes the histidine residue at position 67 of the mature PF4v1 protein.

Typically, the mature PF4v1 protein is as set forth in amino acid sequence SEQ ID NO: 1.

Another aspect of the invention relates to a method for detecting PF4v1 in a biological sample, with the antibody, and/or a fragment thereof according to the invention.

Yet another aspect of the invention relates to an antibody or a fragment thereof according to the invention for treating pathologies that require induction of angiogenesis or diseases that are associated with pathological angiogenesis.

DETAILED DESCRIPTION OF THE INVENTION

Definitions

The term “PF4v1”, as used herein, is intended to encompass all synonyms including, but not limited to, CXCL4L1, PF4var1, PF4ALT and SCYB4V1. The term “PF4v1” refers to both the natural and recombinant versions of the human natural variant of the PF4 protein. The term thus includes naturally occurring PF4v1 and variants and modified forms thereof. The term “mature PF4v1 protein” refers to the mature PF4v1 protein of 70 amino acids which can be obtained by processing of a longer propeptide. An exemplary native mature PF4v1 amino acid sequence is set forth as SEQ ID NO: 1 (mature protein derived from the protein provided in the GenPept database under accession number NP_002611) An exemplary native nucleotide sequence encoding for PF4v1 is provided in GenBank database under accession number NM_002620. It must be further noted that the term “PF4v1” also includes primate natural variants of the PF4 protein. By way of example, primate PF4v1 proteins are provided under GenBank accession number XM_001102971.1 (rhesus monkey) and XP_001156146.1 (chimpanzee).

A “coding sequence” or a sequence “encoding” an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, references to specific proteins (e.g., PF4v1) can include a polypeptide having a native amino acid sequence, as well as variants and modified forms regardless of their origin or mode of preparation. A protein which has a native amino acid sequence is a protein having the same amino acid sequence as obtained from nature (e.g., a naturally occurring PF4v1). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. A native sequence protein includes proteins following post-translational modifications such as glycosylation, or phosphorylation, or other modifications of some amino acid residues.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Function conservative variants of PF4v1 include all variants of PF4v1 which contain the Histidine residue at position 67 and which exhibit substantially the same anti-angiogenic activity as naturally occurring PF4v1. The anti-angiogenic activity of PF4v1 can be assessed by its ability to inhibit proliferation of bovine aortic endothelial (BAE) cells stimulated by FGF-2 as described below.

The term "His67" refers to the amino acid residue which is naturally found at position 67 of the mature PF4v1 protein sequence, for example position 67 of the amino acid sequence as set forth in SEQ ID No. 1. The person skilled in the art will easily construe that said amino acid can be present in fragments of the mature PF4v1 and hence not be found at position 67 of a given protein, whilst still being easily recognized as said amino acid because the environing amino acids.

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

According to the present invention, "antibody" or "immunoglobulin" have the same meaning, and will be used equally in the present invention. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The terms "monoclonal antibody" or "mAb" as used herein refer to an antibody molecule of a single amino acid composition, that is directed against a specific antigen and that is produced by a single clone of B cells or hybridoma.

The expression "recognizes the histidine residue at position 67 of the mature PF4v1 protein", when referring to an antibody, means that said antibody which recognizes PF4v1 does not recognize a variant of PF4v1 in which the histidine residue at position 67 of the mature PF4v1 protein has been replaced by another amino acid residue. Typically, the specificity of said antibody can be verified by dot blot using PF4v1 variants in which the histidine residue at position 67 of the mature PF4v1 has been replaced by another residue, as described in the Examples below.

The terms "neutralizing antibody" or "antibody that neutralizes" as used herein refer to an antibody that blocks or reduces at least one activity of a polypeptide comprising the epitope to which the antibody specifically binds. In certain embodiments, a neutralizing antibody reduces an activity in vitro and/or in vivo. Typically, a neutralizing antibody blocks the anti-angiogenic activity of PF4v1 (which can be assessed by the FGF-2 stimulated proliferation of bovine aortic endothelial (BAE) cells assay as described below).

The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used.

The term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody".

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 and antigen binding activity, which is slightly larger than the Fab bound via a disulfide bond of the hinge region, among fragments obtained by treating IgG with a protease, pepsin.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

The term "hybridoma" denotes a cell, which is obtained by subjecting a B cell prepared by immunizing a non-human mammal with an antigen to cell fusion with a myeloma cell derived from a mouse or the like which produces a desired monoclonal antibody having an antigen specificity.

By "purified" and "isolated" it is meant, when referring to a polypeptide (i.e. the antibody fragment of the invention) or a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a mammal, such as a rodent, a feline, a canine, and a primate. Preferably a subject according to the invention is a human.

Antibodies of the Invention

The present invention provides for isolated neutralizing antibodies or fragments thereof that are directed against PF4v1. In particular, the inventors have developed monoclonal antibodies having specificity for PF4v1 and more particularly an epitope comprising the histidine residue at position 67 of the amino acid sequence of mature PF4v1, as set forth as SEQ ID NO: 1.

The inventors have indeed underlined that only this histidine residue induces the increased anti-angiogenic activity of PF4v1 compared to PF4.

Therefore, the invention relates to an antibody directed against Platelet factor variant 1 (PF4v1), wherein said antibody recognizes the histidine residue at position 67 of the mature PF4v1 protein.

The invention relates to an antibody directed against Platelet factor variant 1 (PF4v1), wherein said antibody recognizes the histidine residue at position 67 of the amino acid sequence SEQ ID NO: 1.

According to one embodiment, said antibody is a monoclonal antibody.

According to an embodiment, the monoclonal antibody of the invention is a murine antibody.

In another embodiment, the monoclonal antibody of the invention is a chimeric antibody, preferably a chimeric mouse/human antibody.

In still another embodiment, the monoclonal antibody of the invention is a humanized antibody. In particular, in said humanized antibody, the variable domain comprises human acceptor frameworks regions, and optionally human constant domain where present, and non-human donor CDRs, such as mouse CDRs as defined above.

The invention further provides fragments of said neutralizing monoclonal antibodies which include but are not limited to Fab, F(ab')2, Fab' and scFv.

Antibodies and fragments thereof of the invention can be used in an isolated (e.g., purified) form or contained in a vector, such as a membrane or lipid vesicle (e.g. a liposome).

Nucleic Acids, Vectors and Recombinant Host Cells

A further aspect of the invention relates to a nucleic acid sequence encoding an antibody of the invention or a fragment thereof.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further aspect of the invention relates to a vector comprising a nucleic acid of the invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR(O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further aspect of the present invention relates to a cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The YB2/0 cell is preferred, since ADCC activity of chimeric or humanized antibodies is enhanced when expressed in this cell.

The present invention also relates to a method of producing a recombinant host cell expressing an antibody of the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Methods of Producing Antibodies of the Invention

Antibodies of the invention and fragments thereof may be produced by any technique known in the art, such as, without limitation, any chemical, biological, genetic or enzymatic technique, either alone or in combination.

Antibodies according to the invention may be derived from a number of species including, but not limited to, rodent (mouse, rat, rabbit, guinea pig, hamster, and the like), porcine, bovine, equine or primate and the like.

Procedures for raising "polyclonal antibodies" are well known in the art. For example, polyclonal antibodies can be obtained from serum of an animal immunized against PF4v1 or a fragment thereof containing His67, which may be produced by genetic engineering for example or by peptide synthesis according to standard methods well-known by one skilled in the art. Typically, such antibodies can be raised by administering PF4v1 or a fragment thereof containing His67 subcutaneously to New Zealand white rabbits which have first been bled to obtain pre-immune serum. The antigens can be injected at a total volume of 100 µl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times at six weeks' interval. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al., 1988.

Laboratory methods for preparing monoclonal antibodies are well known in the art (see, for example, Harlow et al., 1988). Monoclonal antibodies may be prepared by immunizing a mammal such as mouse, rat, primate and the like, with PF4V1 or a fragment thereof containing His67. The antibody-producing cells from the immunized mammal are isolated and fused with myeloma or heteromyeloma cells to produce hybrid cells (hybridoma). The hybridoma producing the monoclonal antibodies are utilized as a source of the desired monoclonal antibody. This standard method of hybridoma culture is described in (Kohler and Milstein, 1975).

Alternatively, the immunoglobulin genes may be isolated and used to prepare a library for screening for specifically reactive antibodies. Many such techniques including recombinant phage and other expression libraries are known to one skilled in the art.

The method for producing antibodies of the invention further comprises the step of selecting antibodies for their ability to recognize the Histidine residue at position 67 of the mature PF4v1 protein by eliminating those antibodies that also bind to a mutant PF4v1 wherein amino acid Histidine 67 has been substituted by another amino acid.

Knowing the amino acid sequence of the desired sequence, one skilled in the art can readily produce said antibodies or fragments thereof, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques as is well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

In particular, the invention further relates to a method of producing an antibody or fragment thereof of the invention, which method comprises the steps consisting of: (i) culturing a transformed host cell according to the invention under conditions suitable to allow expression of said antibody or fragment thereof; and (ii) recovering the expressed antibody or fragment thereof.

Typically, the method of the invention can further contain the steps of verifying that said antibody recognizes the histidine residue at position 67 of the mature PF4v1 protein. This can be done for example by dot blot using PF4v1 variants in which the histidine residue at position 67 of the mature PF4v1 has been replaced by another residue, as described in the Examples below. Typically, the method of the invention can further comprise the step of verifying that said antibody is a neutralizing antibody, i.e. that it blocks the anti-angiogenic activity of PF4v1. This can be performed for example by the proliferation assay using FGF-2-stimulated bovine aortic endothelial cells (BAE) as described in the Examples below.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (Morrison S L. et al. (1984) and patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al. 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with PF4v1 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with PF4v1 with a protease, pepsin. Also, the F(ab')2 can be produced by binding Fab' described below via a thioether bond or a disulfide bond.

The Fab' of the present invention can be obtained treating F(ab')2 which specifically reacts with PF4v1 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (See, e.g., WO98/45322; WO 87/02671; U.S. Pat. No. 5,859,205; U.S. Pat. No. 5,585, 089; U.S. Pat. No. 4,816,567; EP0173494).

Modification of the Antibodies of the Invention

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with ibinding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

The amino acid changes may be achieved by changing codons in the DNA sequence, according to Table 1.

TABLE 1

| Amino acids | Codons | | | | | | |
|---|---|---|---|---|---|---|---|
| Alanine | Ala | A | GCA, | GCC, | GCG, | GCU | |
| Cysteine | Cys | C | UGC, | UGU | | | |
| Aspartic Acid | Asp | D | GAC, | GAU | | | |
| Glutamic acid | Glu | E | GAA, | GAG | | | |
| Phenylalanine | Phe | F | UUC, | UUU | | | |
| Glycine | Gly | G | GGA, | GGC, | GGG, | GGU | |
| Histidine | His | H | CAC, | CAU | | | |
| Isoleucine | Ile | I | AUA, | AUC, | AUU | | |
| Lysine | Lys | K | AAA, | AAG | | | |
| Leucine | Leu | L | UUA, | UUG, | CUA, | CUC, | CUG, CUU |
| Methionine | Met | M | AUG | | | | |
| Asparagine | Asn | N | AAC, | AAU | | | |
| Proline | Pro | P | CCA, | CCC, | CCG, | CCU | |
| Glutamine | Gln | Q | CAA, | CAG | | | |
| Arginine | Arg | R | AGA, | AGG, | CGA, | CGC, | CGG, CGU |
| Serine | Ser | S | AGC, | AGU, | UCA, | UCC, | UCG, UCU |
| Threonine | Thr | T | ACA, | ACC, | ACG, | ACU | |
| Valine | Val | V | GUA, | GUC, | GUG, | GUU | |
| Tryptophan | Trp | W | UGG | | | | |
| Tyrosine | Tyr | Y | UAU | | | | |

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further aspect of the present invention also encompasses function-conservative variants of the antibodies of the present invention.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO 87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Edge, A S et al. 1981. Enzymatic cleavage of carbohydrate moieties on antibodies can be achieved by the use of a variety of endo- and exo-glycosidases as described by Thotakura N R et al. 1987.

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

Detection Methods and Uses

It has been determined that PF4v1 binds to heparin with lower affinity than PF4 on the basis that it eluted at lower concentrations from the heparin-Sepharose column. Such difference in affinity allowed for the first time to purify the natural PF4v1 protein (Struyf et al. 2004). However, such purification procedure is really complex and time consuming since it comprises several steps of chromatography (i.e. heparin-Sepharose affinity chromatography and reversed-phase high-performance liquid chromatography) and also a step of mass spectrometry (Struyf et al. 2007).

Accordingly, the antibody of the invention is useful for the detection and/or purification of PF4v1.

A further aspect of the invention thus relates to the use of an antibody of the invention or a fragment thereof for the detection of PF4v1 in a biological sample. In a preferred embodiment, antibodies of the invention may be labelled with a detectable molecule or substance, such as a fluorescent molecule, a radioactive molecule or any others labels known in the art. Labels are known in the art that generally provide (either directly or indirectly) a signal.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

An antibody of the invention may be labelled with a radioactive molecule by any method known to the art. For example radioactive molecules include but are not limited radioactive atom for scintigraphic studies such as $I^{123}$, $I^{124}$, $In^{111}$, $Re^{186}$ and $Re^{188}$. Antibodies of the invention may be also labelled with a spin label for nuclear magnetic resonance (NMR) imaging (also known as magnetic resonance imaging, mri), such as iodine-123, iodine-131, indium-III, fluorine-19, carbon-13, nitrogen-15, oxygen-17, gadolinium, manganese or iron.

A "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived there from, and the progeny thereof. Therefore, biological samples encompass clinical samples, cells in culture, cell supernatants, cell lysates, serum, plasma, urine, cerebro-spinal fluid, biological fluid, and tissue samples.

The term "detection" as used herein includes qualitative and/or quantitative detection (measuring levels) with or without reference to a control.

In one aspect, the invention is a method for detecting PF4v1 in a biological sample using an antibody of the invention or a fragment thereof. In particular, said method may comprise a step of contacting said biological sample with an antibody of the invention or a fragment thereof.

Therapeutic Methods and Uses

Antibodies of the invention or fragments thereof may be useful for treating any pathology that requires induction of angiogenesis. The antibodies of the invention may be used alone or in combination with any suitable agent.

Thus, an aspect of the invention relates to a method for treating a pathology that requires induction of angiogenesis comprising the administration to a subject in need thereof with a therapeutically effective amount of an antibody or fragment thereof of the invention.

Pathologies that require induction of angiogenesis typically include atherosclerotic diseases, such as coronary heart disease and peripheral arterial disease; wound healing disorders; ischemia; hypertension and diabetes.

The invention relates to an antibody or fragment thereof as described above for treating pathologies that require induction of angiogenesis selected from the group consisting of atherosclerotic diseases, such as coronary heart disease and peripheral arterial disease; wound healing disorders; ischemia; hypertension and diabetes.

The invention relates to an antibody or fragment thereof as described above for use in treating pathologies that require induction of angiogenesis selected from the group consisting of atherosclerotic diseases, such as coronary heart disease and peripheral arterial disease; wound healing disorders; ischemia; hypertension and diabetes.

Antibodies of the invention or fragments thereof may also be useful for treating haematological diseases such as thrombocytopenia, heparin-induced thrombocytopenia (HIT), thrombocytosis, myelodysplastic syndromes, wherein aberrant expression of PF4v1 is observed or wherein PF4v1 plays a pathophysiological role. For example PF4v1 was shown to be upregulated in patients suffering from myelodysplastic disease (Pellagatti et al., 2006) and PF4 knock-out mice present thrombocytemia due to inhibition of megacaryopoiesis (Eslin et al., 2006).

The invention also relates to a method for treating haematological diseases such as thrombocytopenia, heparin-induced thrombocytopenia (HIT), thrombocytosis and myelodysplastic syndromes comprising the administration to a subject in need thereof with a therapeutically effective amount of an antibody of the invention or fragment thereof.

The invention also relates to antibody or fragment thereof as described above for treating haematological diseases such as thrombocytopenia, heparin-induced thrombocytopenia (HIT), thrombocytosis and myelodysplastic syndromes.

The invention also relates to antibody or fragment thereof as described above for use in treating haematological diseases such as thrombocytopenia, heparin-induced thrombocytopenia (HIT), thrombocytosis and myelodysplastic syndromes.

The overexpression of PF4v1 in a number of pathologies enables the specific targeting of pathological cells with an antibody or fragment thereof according to the invention which has been coupled with a cytotoxic agent. Indeed, in a number of diseases, for example cancer; age-related macular dystrophy (AMD) and other hyperproliferative ocular diseases; and chronic inflammatory diseases such as chronic inflammatory, polyarthritis, connective tissue disorders and lupus, there is a local increase in the concentration of secreted PF4v1 in the pathological tissue. Thus, when said pathological tissue is targeted by an antibody or fragment thereof according to the invention coupled with a cytotoxic agent, there is a non-specific but localized destroying of the pathological tissue. The affinity of PF-4v1 with proteoglycans is not as high as for PF-4 but there is still significant binding to glycans. This is evidenced by the fact that PF-4v1 is eluted from the heparin sepharose column at 0.5 M NaCl. This is similar to PDGF-BB which exhibits a heparan sulfate retention sequence that is important for its biological activity.

The present invention provides a method for treating a disease associated with pathological angiogenesis selected from the group consisting of cancer; age-related macular dystrophy (AMD) and other hyperproliferative ocular diseases; and chronic inflammatory diseases such as chronic inflammatory, polyarthritis, connective tissue disorders and lupus, comprising the step of administering an effective amount of an antibody or fragment thereof according to the invention which has been coupled with a cytotoxic agent to a subject in need thereof.

Also provided is an antibody or fragment thereof according to the invention coupled with a cytotoxic agent for the treatment of a disease associated with pathological angiogenesis selected from the group consisting of cancer, age-related macular dystrophy (AMD) and other hyperproliferative ocular diseases and chronic inflammatory diseases.

Also provided is an antibody or fragment thereof according to the invention coupled with a cytotoxic agent for use in the treatment of a disease associated with pathological angiogenesis selected from the group consisting of cancer, age-related macular dystrophy (AMD) and other hyperproliferative ocular diseases and chronic inflammatory diseases.

Typically said antibody or fragment thereof coupled with a cytotoxic agent may be conjugated with a cytokine, a cytotoxic drug or labelled with a cytotoxic radioisotope.

Examples of cytokines which can be coupled with the antibody or fragment thereof according to the invention are IL12 and TNFalpha.

Examples of cytotoxic drugs are platinum salts, taxanes, vinca derivatives and analogues, gemcitabine, methotrexate, doxorubicin, cytotoxin such as *Pseudomonas* exotoxin, g protein, and g protein coupled receptor inhibitors.

Common cytotoxic radioisotopes are, for example, $^{131}$I, $^{90}$Y, $^{77}$Lu, $^{67}$Cu, $^{186}$Re, $^{188}$Re, $^{212}$Bi and $^{213}$Bi.

In the context of the invention, the term "treating" or "treatment", as used herein, means reversing, alleviating, inhibiting the progress of, the pathology to which such term applies, or one or more symptoms of such pathology.

According to the invention, the term "patient" or "patient in need thereof" is intended for a mammal, preferably a human, affected or likely to be affected with a pathology requiring induction of angiogenesis.

By a "therapeutically effective amount" of an antibody of the invention is meant a sufficient amount of the antibody to treat said pathology requiring induction of angiogenesis, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

Pharmaceutical Compositions

The antibodies of the invention or fragments thereof may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits

Finally, the invention also provides kits comprising at least one antibody of the invention. Kits containing antibodies of the invention find use in detecting PF4v1 expression in biological sample. Kits of the invention can contain an antibody coupled to a solid support, e.g., a tissue culture plate or beads (e.g., sepharose beads). Kits can be provided which contain antibodies for detection and quantification of PF4v1 in vitro, e.g. in an ELISA or a Western blot. Such antibody useful for detection may be provided with a label such as a fluorescent or radiolabel.

The invention will further be illustrated by the following figures and examples.

FIGURES

FIG. 1 shows differences between the two chemokines PF4 and PF4v1. PF4 and PF4 v1 differ by only 3 amino acids. However PF4v1 (V1) inhibits much more potently proliferation of endothelial cells than PF4. FIG. 1A shows the comparison of the amino acid sequence of PF4v1 and PF4. FIG. 1B is a graph showing the comparison of the effect of PF4v1 and PF4 on cell proliferation. FIG. 1C presents the different PF4v1/PF4 mutants generated. Results are the means±s.e.m. of three independent experiments performed in triplicate.

FIG. 2 shows the obtention of MabV1, a monoclonal antibody against PF4v1. FIG. 2A shows the fusion PF4v1 peptide which was used for immunizing mice. FIG. 2B Mouse monoclonal antibody for PF4v1 (MabV1, clone 9E11-2D5-2G1) is tested by Dot Blot using PF4 and PF4v1 proteins. Monoclonal Anti-PF4 (Mab PF4) that recognizes both proteins is used as control. FIG. 2C presents a Biacore analysis, antibodies are immobilized, and then PF4 and PF4v1 (V1) are injected at different concentrations.

FIG. 3 shows the epitope characterization of MabV1. FIG. 3A presents a Dot-blot of PF4v1/PF4 mutant proteins using MabV1. Mab PF4 is a control antibody that recognizes PF4 and PF4v1. FIG. 3B represents specific ELISA with MabV1 using PF4v1, PF4, or mutant proteins. MabV1 is immobilized on ELISA plates and polyclonal anti-PF4 antibody (detects all variants) is used for detection. Proteins are all tested at the same concentration (1 ng/ml). Results are the means±s.e.m. of two independent experiments performed in triplicate and expressed as 100% of V1*P<0.01 for V1-E and F4+H versus V1.

FIG. 4 shows the inhibitory activity of MabV1. MabV1 (1 µg/ml) is added in the proliferation assay using FGF-2 stimulated bovine aortic endothelial cells (BAE). The inhibition of proliferation by PF4v1 is specifically blocked by Mabv1. Results are the means±s.e.m. of three independent experiments performed in triplicate.

FIG. 5: Induction of tumor growth by treatment of BxPC3 xenografted mice with the blocking antibody MabV1

Mice (Rag Gamma, n=32, two independent experiments) were sc injected with $3 \times 10^6$ BxPC3 cells and divided in two groups which received 50 µg IgG control antibody (group control, n=16) or 50 µg of blocking antibody MabV1 (group MabV1, n=16). Traitement started at 14 days and antibodies were iv injected twice a week. Tumor dimensions were measured each week and tumor volumes were calculated using the formula: (4/3) ab$^2$ (where a and b are the largest and the smallest radius respectively) (A). On day 46, tumors were resected, and the dimensions were measured to determine the tumor volume more exactly (B), which was calculated by the formula: (4 abc)/3 (a, b, or c, measured radii). Points/Columns, mean tumor sizes (mm$^3$); bars, SEM. (*, p<0.05; **, p<0.01, Mann-Whitney test). Representative transplanted tumors treated with control antibody (top) and MabV1 (bottom) (C). Mice injected with the blocking antibody have larger, cystic tumors. In the control group, the cystic cavity is filled with clear serous fluid, whereas in the group injected with the blocking antibody, the liquid is haemorrhagic and the cavity is filled with serous walls (D). Blood vessels were visualized in frozen tissue sections by staining with anti-CD31 followed by a faint counterstain with Mayer's hematoxylin (E).

Figure 6:
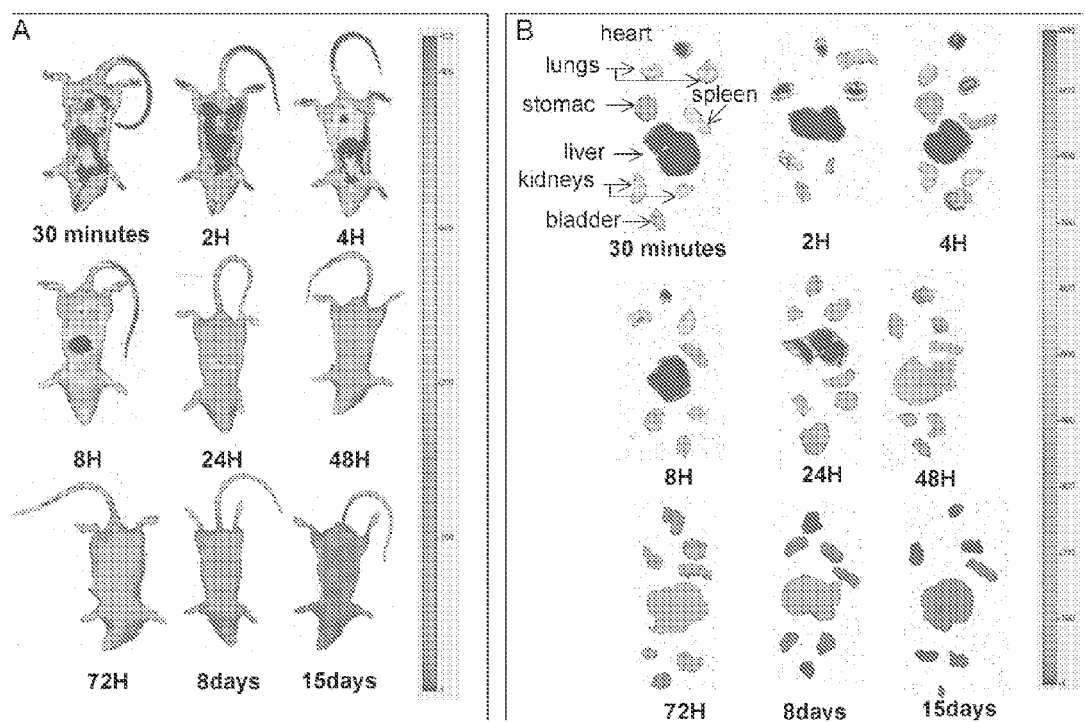

FIG. 6: Clearance profile of MabV1-IRDye™ 800CW from a tumor-negative mouse over a 15-days period. Sterile-filtered MabV1 conjugated to IRDye™ 800CW (25 µg per animal) was injected into the tail vein. Images were then collected at the indicated time points on the Odyssey Imaging System (Licor). Images were normalized to the same LUT with a common minimum and maximum value for visual presentation. (1-400 for whole body A 1-1000 for organes B).

Figure 7:
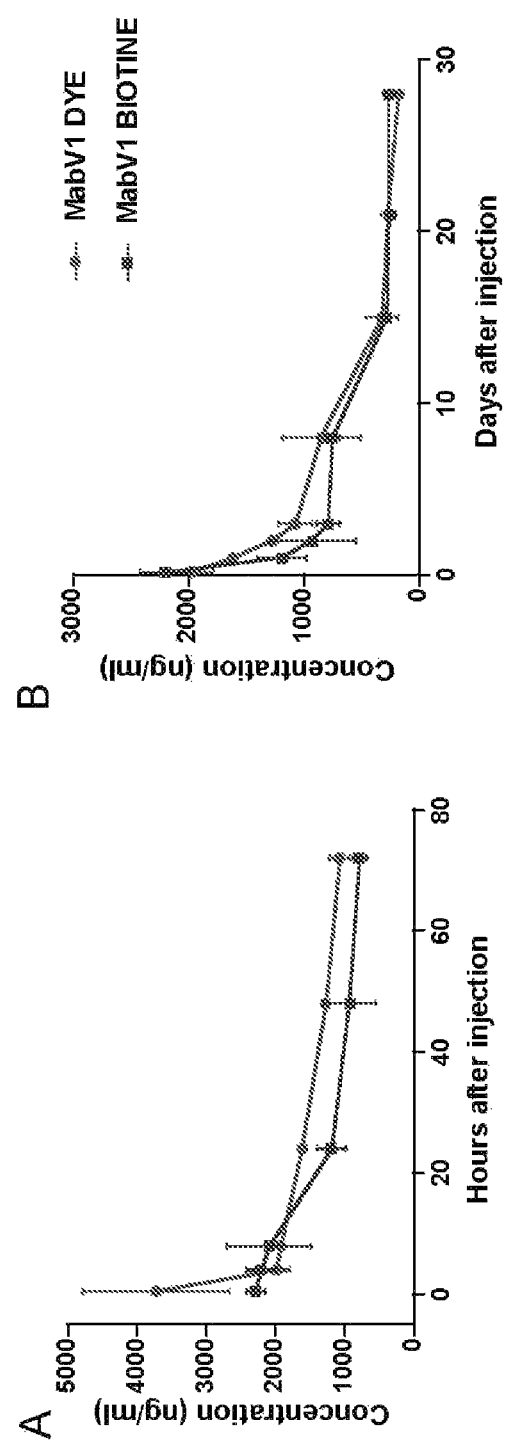

FIG. 7: Plasma concentration of MabV1 conjugated to IRDye or to biotine at different times post-injection.

Blood was collected directly from heart of mice injected with 25 µg of MabV1 labeled with IRDye (Red lines) or with Biotin (blue lines) at different times post-injection (A short period until 72 hours, B long period until 4 weeks). Blood was centrifugated and plasma concentration of MabV1 was assayed by a direct ELISA test.

Figure 8:
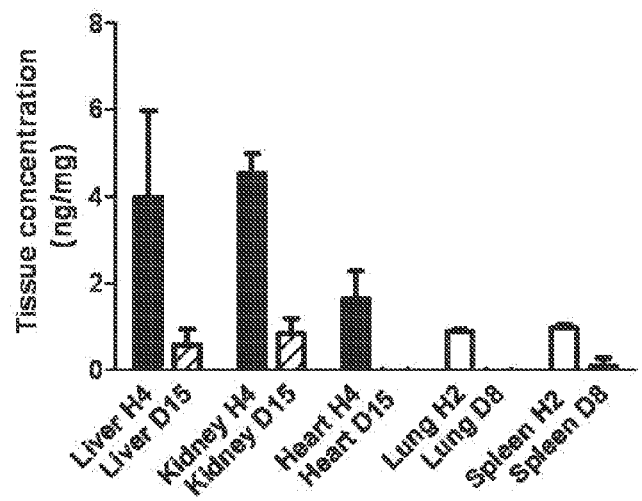

FIG. 8: Determination of tissue concentration of MabV1 in different organes:

Organs were removed from mice injected with IRDye 800CW labeled MabV1 at different times and immediately after imaging were homogenized for determination of MabV1 concentration by a direct ELISA assay.

Figure 9:
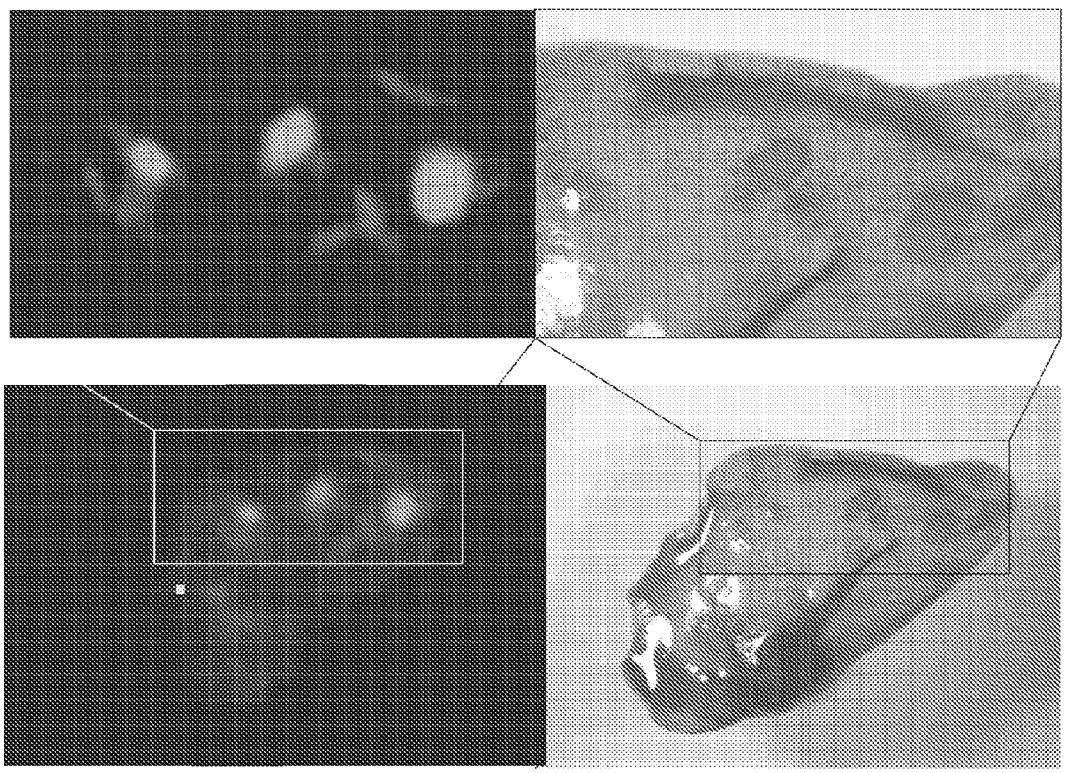

FIG. 9: Targeting of Lung metastasis targeting of MabV1 conjugated to IRdye 800.

Labeled Mabv1 is injected in mice that were iv injected with BXPC3 tumors and lung metastasis (green) are visualized with Odyssey infrared imager (LiCor).

EXAMPLES

Example 1

Characterization of a Monoclonal Antibody Specific for PF4v1 (MabV1)

Material & Methods

Cell culture: BAE cells were grown in DMEM (Invitrogen, Cergy Pontoise, France) containing antibiotics, 1% glutamine, and 10% fetal calf serum or 10% calf serum and were maintained in a 37° C. and 10% CO$_2$.

Plasmids: The coding regions of human PF4/CXCL4 and PF4v1/CXCL4L1 cDNA were cloned from pCDNA-PF4 and pCDNA-PF4v1 in two consecutive steps. First, rather long PF4 and PF4v1 cDNA fragments were amplified by primers binding PF4 and PF4v1 (Full-PF4s and Full-PF4v1s as forward primers; Full-PF4as and Full-PF4v1as as backward primers, Table 2). The amplicons (306 and 315 bp) were cloned into the pSC-A vector (Stratagene). The reconstructed plasmids were verified by DNA sequencing. These constructs were used as a template to amplify the coding region of the mature PF4 and PF4v1 proteins (PF4s and PF4v1s as forward primers; PF4as and PF4v1as as backward primers, Table 2). The purified PCR product was digested with BamH1 and Xho1 restriction enzymes and inserted into the plasmid pGEX-6P-2 (Amersham Biosciences) to generate the pGEX-PF4 and pGEX-PF4v1 expression vectors. Finally, automated DNA Sequencing Analysis checked the nucleotide sequence of the selected clones.

TABLE 2

Primers used in PCR and QuikChange II XL.

| | | 5' -> 3' |
|---|---|---|
| Full-PF4s | SEQ ID No: 2 | AAAAAACTCAAGATCTGGTACCATGAGCTCCGCAGC |
| Full-PF4as | SEQ ID No: 3 | AAAAAACCGCGGCCGCGGATCCCCCTAACTCTCCAAAAGTT |
| Full-PF4v1s | SEQ ID No: 4 | AAAAAACTCAAGATCTGGTACCATGAGCTCCGCAGC |
| Full-PF4v1as | SEQ ID No: 5 | AAAAAACCGCGGCCGCGGATCCCCCTAACTCTCCAAATGTT |
| PF4s | SEQ ID No: 6 | AAACAATTGGTCATATGGAAGCTGAAGAAGATGGGGA |
| PF4as | SEQ ID No: 7 | AAAAAACCGCGGCCGCGGATCCCCCTAACTCTCCAAAAGTT |
| PF4v1s | SEQ ID No: 8 | AAACAATTGGTCATATGGAAGCTGAAGAAGATGGGGA |
| PF4v1as | SEQ ID No: 9 | AAAAAACCGCGGCCGCGGATCCCCCTAACTCTCCAAATGTT |
| M1s | SEQ ID No: 10 | GCTTGGATCTGCAAGCCCCGCTGTACAAGAAAATCATTAA |
| M1as | SEQ ID No: 11 | TTAATGATTTTCTTGTACAGCGGGGCTTGCAGATCCAAGC |
| M2s | SEQ ID No: 12 | GCTGTACAAGAAAATCATTAAGAAACATTTGGAGAGTTAG |
| M2as | SEQ ID No: 13 | CTAACTCTCCAAATGTTTCTTAATGATTTTCTTGTACAGC |
| M3s | SEQ ID No: 14 | GCTGTACAAGAAAATCATTAAGGAACTTTTGGAGAGTTAG |

TABLE 2-continued

Primers used in PCR and QuikChange II XL.

5' -> 3'

| | | |
|---|---|---|
| M3as | SEQ ID No: 15 | CTAACTCTCCAAAAGTTCCTTAATGATTTTCTTGTACAGC |
| M23s | SEQ ID No: 16 | GCTGTACAAGAAAATCATTAAGAAACTTTTGGAGAGTTAG |
| M23as | SEQ ID No: 17 | CTAACTCTCCAAAAGTTTCTTAATGATTTTCTTGTACAGC |

Construction of recombinants pGEX-PF4v1 variants expression vectors: The pGEX-PF4v1 expression vector was used as the DNA template for site-directed mutagenesis procedure using QuikChange II XL kit (Stratagen) (Table 2). Finally, screening of pGEX-PF4v1 mutants clones were performed by DNA sequencing analysis as described earlier.

Production of recombinants PF4v1 and variants in E. coli: E. coli BL21 (DE3) transformed with the pGEX-6P-2 (GST-fusion expression vector, Amersham) recombinant vector containing the different cDNAs described before, were grown in 100 ml LB with 100 μg/ml ampicillin. After the $OD_{600nm}$ reached 0.3-0.5, the expression of the fusion protein was induced by the addition with shaking of 0.5 mmol/L isopropyl-1-thio-β-D-galactopyranoside (IPTG) (Euromedex). Cultures were grown overnight at 220 rpm and 25° C. The IPTG-induced test cultures and the IPTG-induced control culture containing the empty vector pGEX-6P-2 were collected by centrifugation at 5000 r/min for 15 minutes at 4° C. The pellets were resuspended in 10 volumes of lysis buffer containing PBS 1× (10 mM $Na_2HPO_4$, 1.8 mM $KH_2PO_4$, 140 mM NaCl, 2.7 mM KCl, pH 7.3, Lonza), 1 mg/ml lysozyme (Sigma) and cocktail inhibitor protease (Roche). Cells were lysed by freeze/thaw, using liquid nitrogen, followed by sonication (six 30-s sonication steps) in an ice bath. For complete fragmentation of DNA, 5 g/ml DNase I (Sigma) was added and stirred on ice for 15 min. The cell debris was removed by centrifugation at 12 000 r/min for 30 minutes at 4° C. and the supernatant was collected.

Affinity chromatography step for GST-PF4v1 recombinant protein purification: The supernatant containing the soluble GST-PF4v1 or GST-PF4 (or an another variant) recombinant protein was loaded on a GSTrap HP affinity column (5 ml; Amersham Biosciences) pre-equilibrated with PBS IX at a flow rate of 1 ml/min at room temperature. The bound material was washed with PBS IX until the absorbance at an OD of 280 nm returned to baseline. Once the baseline was stable, elution of the bound GST-PF4v1 recombinant protein was carried out using ten column volumes of elution buffer (PBS IX, 20 mM reduced glutathione, pH 8.0) at a 1 ml/min flow rate. The eluted fractions containing the GST-PF4v1 recombinant protein were pooled. The purification stages and affinity chromatographic profiles were analyzed by Coomassie Blue-stained (Biorad) SDS-PAGE gels and by western blot analysis.

Cell viability assay: BAE cells were plated for 24 h in flat-bottomed 96-well plates at $5 \times 10^3$ cells/well. Following overnight serum starvation, cells were treated in triplicate for 48 h with 10 ng/ml of recombinant FGF2 and in the presence or absence of different concentrations of recombinants proteins. Cell viability was measured at 490 nm using the CellTiter 96 $AQ_{ueous}$ One Solution cell proliferation assay (Promega Corp.) following the manufacturer's instructions.

SPR (surface plasmon resonance): Real-time binding experiments were performed with a BIAcore 3000 biosensor instrument (BIAcore AB) and quantified in terms of resonance units (RU) (1000 RU=1 ng of protein bound/$mm^2$ of flow cell surface) (Ferjoux et al, 2003). Antibodies were immobilized on a carboxymethylated dextran chip (chip CM5, BIAcore AB). Antibodies (10000 RU) were crosslinked on flow cell 2 and flow cell 3, whereas flow cell 1 was activated and deactivated as a nonspecific interaction reference. Soluble ligands (500-1000 nM) were injected at a flow rate of 30 μl/min, exposed to the surface for 600 s (association phase) followed by a 300 s flow running during which the dissociation occurred. Sensorgrams are representative of specific interactions (differential response) where non-specific binding that occurred on flow cell 1 was deduced from binding that occurred on flow cell 2 and 3. Results are expressed as resonance units (RU) as a function of time in seconds.

ELISA: PF4, PF4v1 and variants were measured using the commercial PF4-ELISA kits (R&D Systems). PBS was used as blank. After protein quantification, the recombinants proteins were measured again using the commercial PF4-ELISA except that the first mouse monoclonal PF4 antibody was substituted by the mouse monoclonal PF4v1 antibody (clone 9E11-2D5-2G1). Assays were performed in triplicate and results analyzed using the Softmax Pro4.0 software (Molecular Devices).

Dot blot analysis: Mouse monoclonal antibody for PF4v1 (MabV1, clone 9E11-2D5-2G1) was tested and its epitope was evaluated by performing a dot blot analysis using recombinants proteins PF4 and PF4v1. 0.5 μg of protein were spotted onto a nitrocellulose membrane using a microfiltration blotting apparatus. After washing twice with TBST for 5 min, the membrane was incubated with 3% nonfat milk TBST for 30 min. After washing three times with TBST for 5 min, the membrane was incubated with specific antibodies at a dilution of 1:1000. The following antibodies were used: anti-PF4 monoclonal antibody (mAb; R&D Systems, Minneapolis, Minn., clone 170106, 7 μg/mL), anti-PF4v1 monoclonal antibody (MabV1, clone 9E11-2D5-2G1). HRP-labeled secondary antibodies were revealed by the ECL system.

Statistical analysis: Experiments were performed at least three times. Statistical analysis was performed by unpaired t-test. All values are mean±s.e.m.

Results

There is only three amino acid difference in the C-terminal region between PF4 and PF4v1 (FIG. 1). When tested for biological activity (proliferation assay on bovine aortic endothelial cells), PF4v1 is 50 times more active. We have generated several mutants for PF4 and PF4v1 that were tested for antibody reactivity.

We then generated a monoclonal antibody specific for PF4v1 (MabV1) (FIG. 2). A PF4v1 fusion peptide was used for immunizing mice. We then tested the hybridoma supernatants for reactivity against PF4 or PF4v1 by dot blot (MabV1, clone 9E11-2D5-2G1). As seen in FIG. 3 b the monoclonal antibody from clone 9E11-2D5-2G1 only cross reacted with PF4v1 but not with PF4. On the other hand, the anti-PF4 anti-body cross reacted with both PF4 and PF4v1.

We next performed Biacore analysis. The antibodies are immobilized and then PF4 and PF4v1 are injected at different concentrations. As seen the monoclonal antibody against PF4v1 only recognizes PF4v1 but not PF4.

We next characterized the reactivity of the monoclonal antibody (FIG. 3). Dot-blot of PF4v1/PF4 mutant proteins were performed using MabV1. Mab PF4 was used as a control which recognizes both PF4 and PF4v1. As seen in FIG. 3 when Histidine is mutated in PF4v1 the antibody does not recognize the molecule any more. On the contrary, when Histidine is introduced instead of Leucine in PF4 the antibody recognizes again the mutated PF4.

We next studied the neutralizing activity of MabPF4v1 (FIG. 4). MabV1 (1 µg/ml) was added in the proliferation assay using FGF-2-stimulated bovine aortic endothelial cells (BAE). As seen in FIG. 4, inhibition of proliferation by PF4v1 is specifically blocked by MabV1. This indicates that MabV1 blocks the function of PF4v1.

Example 2

In Vivo Studies Using MabV1 for Targeting Tumors

Material & Methods
Labeling of MabV1 with IRdye.

Monoclonal antibody against CXCL4L1 (MabV1) was labeled with IRDye 800CW (Protein Labeling Kit-HighMW#928-38040, LI-COR®, Lincoln, Nebr.) following the manufacturer's instructions. The conjugate was dialyzed extensively against phosphate buffered saline to remove excess of nonreacted dye. The labeled MabV1 bound 2 dye molecules per mole of protein and do not lose its initial activity. The IRdye-MabV1 was used in studies of its biodistribution, pharmacokinetics and tolerance in mice and also in the study of targeting tumors expressing CXCL4L1.

Labeling of MabV1 with Biotin.

MabV1 antibody is labeled with biotin using the kit sulfo-NHS-LC-Biotin (PIERCE, Rockford, Ill.) and following the manufacturer's instructions.

Clearance Kinetic of MabV1 Conjugated to IRDye.

To determine the clearance rate and possible non-specific binding of the antibody, Rag Gamma mice (n=50) received an IV injection of 25 µg of IRdye-MabV1 into the tail vein. At different times post-injection animals were imaged with the Odyssey Imaging System (LI-COR®) equipped with the MousePOD™ and until there was no detectable signal above background. After imaging, blood was collected intracardially and the organs were removed, scanned on the Odyssey Imaging System and homogenized for determination of MabV1 concentration by an indirect ELISA assay.

Indirect ELISA Assay

Recombinant CXCL4L1 protein diluted in a coating solution is immobilized on a microplate. After several steps of washing and blocking, plasma samples and organs lysates are added to the plate. For samples containing MabV1 conjugated to biotin, the result is obtained directly after adding streptavidin-HRP and a substrate solution (TMB) on a microplate reader set to 450 nm. While for samples containing MabV1 an additional step with a biotinylated anti-mouse antibody is required.

Mice Treatment.

Rag Gamma mice were subcutaneously injected with $3 \cdot 10^6$ BxPC3 cells and divided in two groups which received 50 µg IgG control antibody (group control, n=16) or 50 µg of blocking antibody MabV1 (group MabV1, n=16). Treatment started at 14 days and antibodies were iv injected twice a week. Tumor dimensions were measured each week and tumor volumes were calculated using the formula: (4/3) ab2 (where a and b are the largest and the smallest radius respectively). Mice were sacrificed at 7 weeks, tumors were resected, measured and stored in liquid nitrogen before immunohistochemistry studies.

In Vivo Tumor Targeting.

IRdye-MabV1 antibody was injected into the tail vein of mice with subcutaneous BxPC3 tumors. 6 days after injection, animals were euthanized and the tissues were removed and imaged on the Odyssey Imaging System. Immediately after imaging organs were frozen and cut into 10 and 40 µm sections for immunohistochemistry studies and odyssey imaging respectively.

Results

The inventors have shown that the antibody according to the invention (MabV1) blocks the function of PF4v1 in vivo and is able to induce angiogenesis in vivo (FIG. 5).

Clearance of MabV1 and conjugated MabV1 was analyzed in vivo (FIGS. 6 to 8). Furthermore, the inventors have shown that MabV1 is able to target tumors in vivo. This provides an indication that, when coupled to a cytotoxic agent, the antibody of the invention can be useful in the treatment of a disease associated with pathological angiogenesis such as cancer.

REFERENCES

Auguste P, Lemiere, S, Larrieu-Lahargue, F, Bikfalvi A. Cirtical Reviews in Oncology/Hematology. 2005 54:53-61.

Bikfalvi A, Bicknell, R. Recent advances in angiogenesis, anti-angiogenesis and vascular targeting. Trends in Pharmacological Sciences. 2002 December; 23: 576-582.

Brady G, Jantzen H M, Bernard H U, Brown R, Schutz G, Hashimoto-Gotoh T. New cosmid vectors developed for eukaryotic DNA cloning. Gene. 1984 February; 27(2):223-32.

Edge A S, Faltynek C R, H of L, Reichert L E Jr, Weber P. Deglycosylation of glycoproteins by trifluoromethanesulfonic acid. Anal Biochem. 1981 Nov. 15; 118(1):131-7.

Don E. Eslin, Chunyan Zhang, Kathleen J. Samuels, Lubica Rauova, Li Zhai, Stefan Niewiarowski, Douglas B. Cines, Mortimer Poncz, and M. Anna Kowalska, Blood, 15 Nov. 2004, Vol. 104, No. 10, pp. 3173-3180.

Eisman R, Surrey S, Ramachandran B, Schwartz E, Poncz M. Structural and functional comparison of the genes for human platelet factor 4 and PF4alt. Blood 1990; 76: 336-344.

Gillies S D, Morrison S L, Oi V T, Tonegawa S. A tissue-specific transcription enhancer element is located in the major intron of a rearranged immunoglobulin heavy chain gene. Cell. 1983 July; 33(3):717-28.

Kuwana Y, Asakura Y, Utsunomiya N, Nakanishi M, Arata Y, Itoh S, Nagase F, Kurosawa Y. Expression of chimeric receptor composed of immunoglobulin-derived V regions and T-cell receptor-derived C regions. Biochem Biophys Res Commun. 1987 Dec. 31; 149(3):960-8.

Maione T E, Gray G S, Petro J, Hunt A J, Donner A L, Bauer S I, Carson H F, Sharpe R J. Inhibition of angiogenesis by recombinant human platelet factor-4 and related peptides. Science 1990; 247: 77-79.

Mason J O, Williams G T, Neuberger M S. Transcription cell type specificity is conferred by an immunoglobulin VH gene promoter that includes a functional consensus sequence. Cell. 1985 June; 41(2):479-87.

Miyaji H, Mizukami T, Hosoi S, Sato S, Fujiyoshi N, Itoh S. Expression of human beta-interferon in Namalwa KJM-1 which was adapted to serum-free medium. Cytotechnology. 1990 March; 3(2):133-40.

Mizukami T, Itoh S. A new SV40-based vector developed for cDNA expression in animal cells. J Biochem (Tokyo). 1987 May; 101(5):1307-10.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Neuberger M S, Williams G T, Fox R O. Recombinant antibodies possessing novel effector functions. Nature. 1984 Dec. 13-19; 312(5995):604-8.

O'Hare K, Benoist C, Breathnach R. Transformation of mouse fibroblasts to methotrexate resistance by a recombinant plasmid expressing a prokaryotic dihydrofolate reductase. Proc Natl Acad Sci USA. 1981 March; 78(3): 1527-31.

Padlan E A. A possible procedure for reducing the immunogenicity of antibody variable domains while preserving their ligand-binding properties. Mol Immunol. 1991 April-May; 28(4-5):489-98.

Pellagatti, A, Cazzola, M, Giagounidis A, Malcovati, L, Della Porta M, Killick S, Campbell, L, Wang, L, Langford, C, Fidler, C, Oscier, D, Aul, C, Wainscoat, J, Boultwood, J. Gene expression profiles of CD34+ cells in myelodysplastic syndromes: involvement of interferon-stimulated genes and correlation to FAB subtype and karyotype. Blood. 2006, 108(1):337-345

Riechmann L, Clark M, Waldmann H, Winter G Reshaping human antibodies for therapy. Nature. 1988 Mar. 24; 332 (6162):323-7.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Struyf S, Burdick M D, Proost P, Van Damme J, Strieter R M. Platelets release CXCL4L1, a nonallelic variant of the chemokine platelet factor-4/CXCL4 and potent inhibitor of angiogenesis. Circ Res. 2004 Oct. 29; 95(9): 855-7.

Struyf S, Burdick M D, Peeters E, Van den Broeck K, Dillen C, Proost P, Van Damme J, Strieter R M. Platelet factor-4 variant chemokine CXCL4L1 inhibits melanoma and lung carcinoma growth and metastasis by preventing angiogenesis. Cancer Res. 2007 Jun. 15; 67(12):5940-8.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6):805-14.

Thotakura N R, Bahl O P. Enzymatic deglycosylation of glycoproteins. Methods Enzymol. 1987; 138:350-9.

Urlaub G, Chasin L A. Isolation of Chinese hamster cell mutants deficient in dihydrofolate reductase activity. Proc Natl Acad Sci USA. 1980 July; 77(7):4216-20.

The invention claimed is:

1. A pharmaceutical composition comprising a monoclonal antibody or a fragment thereof directed against human Platelet factor variant 1 (PF4v1) together with a pharmaceutically acceptable carrier, wherein said antibody or said fragment thereof:
   recognizes the histidine residue at position 67 of the mature human PF4v1 protein, and
   blocks the anti-angiogenic activity of human PF4v1.

2. The pharmaceutical composition according to claim 1 wherein said antibody is a murine antibody.

3. A method for treating a pathology that require induction of angiogenesis selected from the group consisting of atherosclerotic diseases, such as coronary heart disease and peripheral arterial disease; wound healing disorders; ischemia; hypertension and diabetes comprising administering to a subject in a need thereof the pharmaceutical composition according to claim 1.

4. A method for treating haematological diseases such as thrombocytopenia, heparin-induced thrombocytopenia (HIT), thrombocytosis and myelodysplastic syndromes comprising administering to a subject in a need thereof the pharmaceutical composition according to claim 1.

5. A method for treating disease associated with pathological angiogenesis selected from the group consisting of cancer, age-related macular dystrophy (AMD) and other hyperproliferative ocular diseases and chronic inflammatory diseases comprising administering to a subject in a need thereof the pharmaceutical composition according to claim 1,
   wherein said antibody or said fragment thereof is coupled with a cytotoxic agent.

* * * * *